United States Patent [19]
Hayes et al.

[11] Patent Number: 5,658,802
[45] Date of Patent: Aug. 19, 1997

[54] METHOD AND APPARATUS FOR MAKING MINIATURIZED DIAGNOSTIC ARRAYS

[75] Inventors: Donald J. Hayes, Plano; David B. Wallace, Dallas; Christopher J. Frederickson, Little Elm, all of Tex.

[73] Assignee: MicroFab Technologies, Inc., Plano, Tex.

[21] Appl. No.: 524,781

[22] Filed: Sep. 7, 1995

[51] Int. Cl.[6] .................................................. G01N 33/543
[52] U.S. Cl. .................... 436/518; 436/501; 435/317.1; 435/286.3; 435/286.4; 435/287.2; 435/287.3; 427/2.13; 417/413.2
[58] Field of Search ...................... 435/317.1, 285; 427/2.13; 417/413.2; 436/501, 518

[56] References Cited

U.S. PATENT DOCUMENTS

| | | | |
|---|---|---|---|
| 4,074,284 | 2/1978 | Dexter et al. | 346/140 R |
| 4,183,031 | 1/1980 | Kyser et al. | 346/140 R |
| 4,412,232 | 10/1983 | Weber et al. | 346/140 R |
| 4,506,276 | 3/1985 | Kyser et al. | 346/140 R |
| 4,713,347 | 12/1987 | Mitchell | 436/501 |
| 4,815,843 | 3/1989 | Tiefenthaler et al. | 356/128 |
| 4,908,112 | 3/1990 | Pace | 204/299 |
| 5,071,248 | 12/1991 | Tiefenthaler et al. | 356/128 |
| 5,094,594 | 3/1992 | Brennan | 417/322 |
| 5,272,081 | 12/1993 | Weinreb et al. | 435/240.1 |
| 5,421,071 | 6/1995 | Kanegae | 29/25.35 |
| 5,443,508 | 8/1995 | Giampapa | 623/11 |
| 5,474,796 | 12/1995 | Brennan | 427/2.13 |

OTHER PUBLICATIONS

Kricka, L J, Clin. Chem. (United States) Mar. 1994 40(3) pp. 347–357.

Primary Examiner—James C. Housel
Assistant Examiner—Ginny Allen Portner
Attorney, Agent, or Firm—Harris, Tucker & Hardin, P.C.

[57] ABSTRACT

Arrays of electro-mechanical dispensers are used to form extremely small drops of fluid and locate them precisely on substrate surfaces in miniature arrays. The printed arrays may consist of DNA, immunoassay reagents or the like. A positioning support such as an X-Y table moves the dispensing devices and substrate surfaces relative to each other to locate the drops on the substrates in predetermined patterns. Arrays of probes as dense as one thousand per square centimeter with center-to-center spacing as small as twenty-five micrometers are formed.

29 Claims, 3 Drawing Sheets

METHOD AND APPARATUS FOR MAKING MINIATURIZED DIAGNOSTIC ARRAYS

This invention relates to miniature printed arrays. More particularly, it relates to using a plurality of programmably controlled liquid ejection devices to form and arrange deposits of large numbers of very small discrete drops of liquids such as DNA or immunoassay reagents and the like on solid supports in predetermined patterns to form miniature diagnostic arrays.

Diagnostic arrays are used in biomedical testing, research, etc., to identify unknown samples of materials such as DNA, antibodies and the like. In the typical process, a diagnostic test strip array is prepared by depositing a number of discrete drops of liquids at known points on a solid substrate to form a predetermined pattern (array) of diagnostic probes. Each liquid deposit or probe has a known tendency to react with a particular substance. After the test strip array is prepared, a sample of an unknown substance is labeled using conventional methods. For example, the sample may be mixed with a radioactive or fluorescent substance or with a substance exhibiting certain electrical or magnetic characteristics. The test strip is then exposed to the labeled sample, thus allowing the sample to react with one or more probes on the test strip.

After an appropriate exposure period, the test strip is cleaned to remove all the sample except that portion which has reacted with a probe. The test strip is then examined to locate the point on the strip which exhibits the characteristics of the labeling substance (radioactivity, fluorescence, changes in electrical or magnetic properties, etc.) Since the location and identity of each probe on the test strip is known, the identity of the unknown sample is determined by determining which substances react with the probe located at the point exhibiting the characteristics of the label.

In the biomedical field, almost all conventional apparatus used to deposit microliter and sub-microliter drops of fluid onto a substrate employ positive displacement methods. Such positive displacement systems may be manual or automated but are generally limited in dispensing frequency to a few events per second. The most common technique used is the precise translation of a piston in a tube similar to a manually operated syringe.

The accuracy of these systems becomes poor below the 100 nl (300 µm diameter droplets) range because of surface tension effects which vary with droplet diameter. These effects can cause a significant portion of the fluid to adhere to the dispenser tip and result in loss of precision. The amount which adheres to the dispenser tip may vary from one dispensing event to the next and any buildup on the dispensing tip will exacerbate this problem. The drop volume may also fluctuate due to variations in the way the dispensed fluid separates from the fluid remaining in the dispensing tip.

Separate technological sectors (i.e., outside the biomedical field) have developed other means for accurately dispensing small drops of liquid and depositing them onto solid substrates. For example, ink jet printers utilize piezoelectric dispensers to dispense liquid drops at rates of up to at least 2,000 drops per second. In one such system (known as a continuous device) a fluid under pressure issues from an orifice in a dispenser while a piezoelectric crystal attached to the dispenser induces pressure oscillations in the fluid causing the fluid stream to break into drops after issuing from the dispenser. The drops form in the presence of an electrostatic field and thus acquire an electric charge. As the drops continue toward the substrate, they pass through another electrostatic field which interacts with their acquired charge to deflect them to a desired location.

In another ink jet system fluid from a reservoir is fed into a dispenser and a piezoelectric crystal directly or indirectly coupled to the fluid responds to a voltage pulse to induce a volume change in the dispenser, thus causing a drop of fluid to issue from an orifice toward a substrate. In this type of dispenser (known as a drop-on-demand device) a drop is formed only in response to a predetermined voltage pulse.

In addition to using piezoelectric effects, ink jets may also use heat to form and propel drops of fluid. Thermal ink jets heat a fluid so rapidly that the fluid vaporizes. Rapid volumetric changes provide the impetus for propelling drops of fluid or ink from the dispenser. Thermal ink jets, however, are very stressful on the dispensed fluid and the fluid must not be too aggressive to the heater element. Because of these constraints, thermal ink jets are generally unsuitable for dispensing applications other than those where the composition of the ink can be carefully controlled.

U.S. Pat. No. 4,877,745 to Hayes, et al. shows a dispensing system having several fluid dispensers and a plurality of moveable fluid receptacles wherein the fluid dispensers are stationary and oriented to dispense fluid into the receptacles moving by dispensers. Hayes, et al. also disclose a system employing a single fluid dispenser mounted to an X-Y plotter. The dispenser ejects fluid toward a printing medium such as filter paper and an X-axis motor positions the dispenser while a Y-axis motor positions the paper to locate the fluid drops on the paper.

In all the forgoing systems a number of fluid reservoirs are provided which is equal to the number of fluid dispensers and each fluid dispenser is fed by a single reservoir. None provide for connecting multiple reservoirs to each fluid dispenser. The number of fluids dispensable by each system is thus limited by the number of dispensers.

In accordance with the present invention methods and apparatus are provided for forming diagnostic arrays having large numbers of probes deposited in close proximity to each other on a solid substrate. Ink jet dispenser technology ejection devices are used to deposit small drops of liquid on a solid substrate at rates much more rapidly than achievable with positive displacement devices. Each ejection device is either connectable to a plurality of reservoirs or is combined with a dedicated reservoir to form an assembly which is removable during a manufacturing sequence. Thus numerous liquids can be dispensed to form a large number of different types of probes on a single test strip, if desired, so that the test strip can be used to perform numerous tests. The invention thus provides a highly accurate, rapid and repeatable method of placing extremely small drops (10 pl to 1 nl) of fluid reagent on substrates to form diagnostic arrays. By using such small drops and accurately positioning them on the substrate, test strips can be formed which have a larger number of probes located within a smaller area than is achievable with prior methods. Use of extremely small drops also minimizes costs by minimizing the quantity of expensive reagent materials required to form the diagnostic array and allowing use of extremely small quantities of unknown substances. Various other features and advantages of the invention will become more readily understood from the following description taken in connection with the appended claims and attached drawing in which:

The invention is described herein by showing various examples of how the invention can be made and used. Like reference characters are used throughout the several views of drawing to indicate like or corresponding parts.

In practicing the preferred method of the invention, a substrate is positioned on a substrate support and a plurality of electro-mechanical fluid dispensers (hereinafter referred to as "ejection devices") are arranged and fixed in spatial relationship relative to each other and oriented to align their outlets toward the surface of the substrate. Fluids are held in a plurality of separate reservoirs and a fluid handling system selectively places the fluids in communication with the ejection devices. A transducer selectively activates each ejection device to propel drops of fluid toward the substrate in response to activation signals. By controlling the relative positions of the ejection devices and the substrate, a predetermined pattern of discrete probes is printed onto the substrate to produce a diagnostic array. Although ejection devices based on any of the ink jet systems heretofore discussed might be used, continuous devices are typically more complex than drop-on-demand devices and thermal devices are too harsh on the dispensed material. Consequently, drop-on-demand devices are presently considered the most practical and have been found to accurately and repeatably print drops of various fluids on solid substrates. The drops adhere to the substrate in the form of discrete diagnostic probes which are arranged in predetermined patterns or arrays by a high accuracy positioning system. These diagnostic arrays may be subsequently exposed to an unknown substance which has been labeled as heretofore described and then examined to determine which of the probes has reacted with the unknown substance.

The dispensing apparatus can dispense a variety of liquid reagents to form a variety of probes. For example, the liquids may contain DNA molecules, peptides, antibodies, antigens, enzymes and entire cells. Furthermore, the apparatus can dispense presynthesized probes such as a selected portion of a DNA molecule or the materials used to synthesize the probe on site. The apparatus can also dispense activator or inhibitor fluids. An activator fluid is one which makes coupling to the substrate possible or causes a synthesis reaction with a previously deposited reagent. An inhibitor fluid protects an area on the substrate to prevent the material in the area from reacting. It is to be understood that the term "reagent" as used herein includes any of the fluids or liquids hereinabove discussed.

Figure 1:
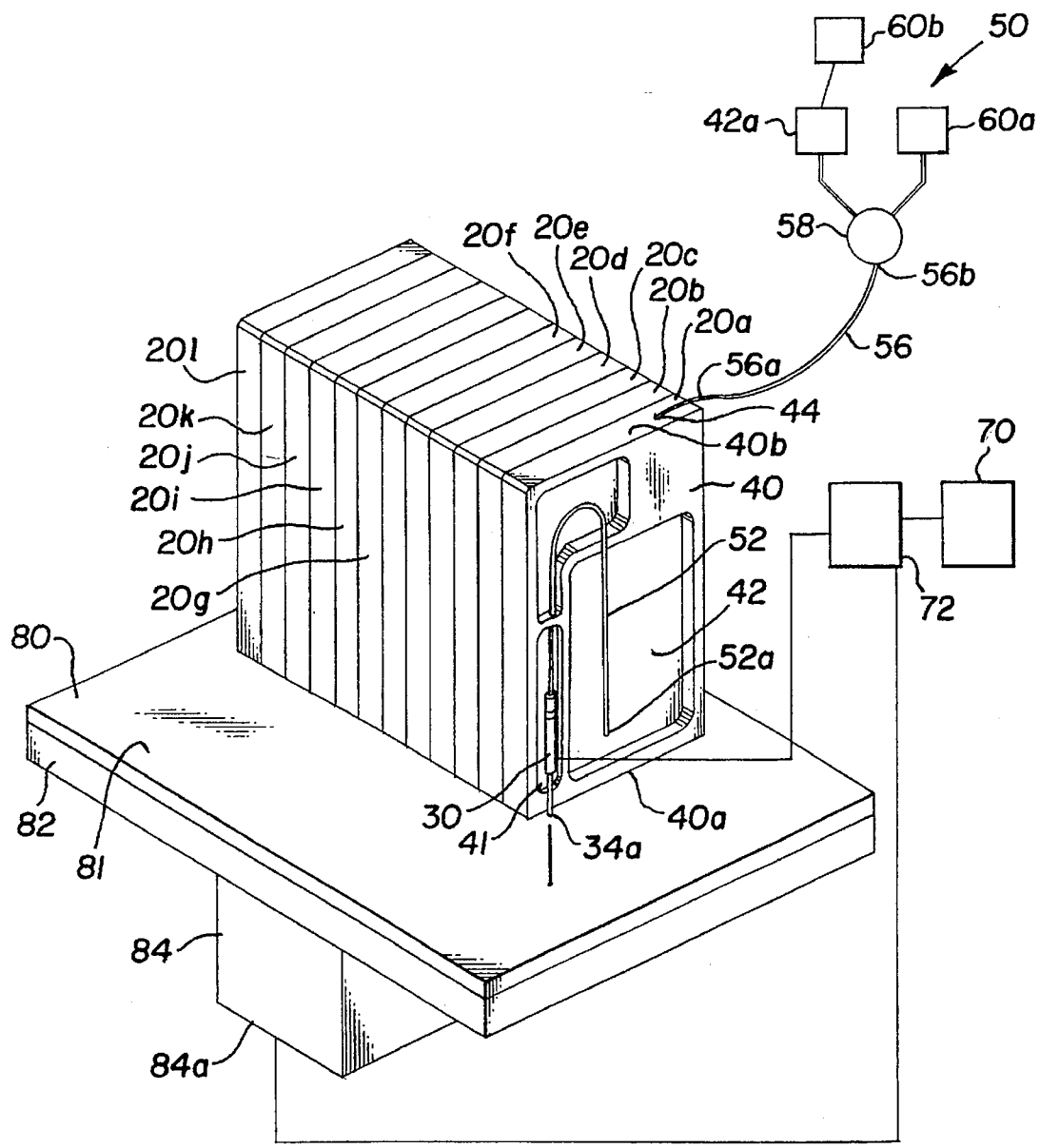
FIG. 1 is a schematic illustration of apparatus employing a plurality of ejection devices arranged to form printed arrays in accordance with the invention.

In FIG. 1 the reference numeral 10 generally indicates apparatus for practicing a preferred method of the invention. Apparatus 10 includes a set or block of fluid dispenser assemblies 20a–20l, each of which comprises a housing 40 which includes an electro-mechanical ejection device 30 and a reservoir 42 in communication with a fluid handling system 50.

Figure 2:
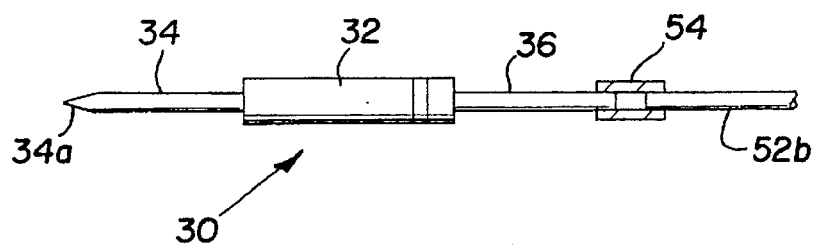
FIG. 2 is a sectional view of an ejection device as shown in FIG. 1.

Ejection device 30 comprises an electro-mechanical transducer 32 such as a piezoelectric, electrostrictive or magnetic device. A typical ejection device employing a piezoelectric crystal transducer is illustrated in FIG. 2. The device 30 includes a nozzle 34 having an outlet or orifice 34a extending from one end of a transducer 32 which is in fluid communication with inlet 36 in the opposite end of transducer 32. Each device 30 is contained within a housing 40 which has first and second ends 40a and 40b and includes a chamber 41 adapted to support the ejection device 30 with its outlet 34a extending from first end 40a. Housing 40 also defines a reagent reservoir 42 therein with a fill port 44 on second end 40b to provide access to the reservoir. The fill port 44 is preferably a valve which maintains reservoir 42 at atmospheric pressure. Alternatively, the fluid dispenser assembly may comprise a two-part housing wherein one part supports the ejection device and a detachable second part serves as a reservoir. Tubing 52, having a first end 52a located in reagent reservoir 42 and a second end 52b connected to inlet 36, conducts fluid from reservoir 42 to the ejection device 30. The fluid handling system 50 comprises tubing 56 having a first end 56a (which is preferably removeably connected to housing 40 at fill port 44) and a second end 56b connected to a solenoid valve 58 which is operable to place either positive pressure supply 60a or reagent reservoir 42a and positive pressure supply 60b in communication with reservoir 42.

The term "positive pressure supply" as used herein generally refers to compressed air but may include any pressurized fluid or any apparatus used to increase the pressure of the various fluids to above atmospheric. The positive pressure is used to move fluids throughout the various components of the apparatus and may also be used to clear obstacles from the tubing, valves, etc. It will be recognized that the positive pressure supplies described herein may be replaced with negative pressure supplies (vacuum) at the same or different points within the various arrangements to serve the same purpose. Similarly, negative pressure supplies described herein may be replaced with positive pressure supplies.

Outlet 34a is sized to provide drops having a volume between about 10 pl to 1 nl. The drop size may be varied by changing the activation signals provided by drive electronics 72 and integral multiples of the single drop volume may be dispensed at rates of up to eight kilohertz. Large changes in drop size may require changing the size of outlet 34a.

As illustrated in FIG. 1, twelve dispenser assemblies 20a–20l are arranged in a set-with their outlets 34a fixed in spatial relationship relative to each other. Each dispenser assembly is connected to a fluid handling system as hereinbefore described.

Substrate 80, having a major face or surface 81, is mounted on substrate support 82 which is supported on a positioning support 84. The term "substrate surface" includes surfaces which are either porous or impermeable to the fluids. The surface may be smooth or uneven such as a surface with depressions found therein. Examples of suitable substrates are patterned devices resembling integrated circuits and flex circuits which are fabricated using semiconductor fabrication methods; un-patterned sheets (with or without alignment marks); and un-patterned material on a roll (with or without alignment marks).

The term "positioning support" as used herein refers to apparatus for causing relative movement between ejection devices 30 and substrate 80. The positioning support may comprise a first positioning system (which moves the substrate 80), second positioning system (which moves the ejection device 30), or both. Thus, it is to be understood that when the movement of the substrate relative to the devices is specified or described, such movement is equivalent to moving the ejection devices relative to the substrate.

The first and second positioning systems are preferably conventional precision apparatus such as X-Y positioning tables (for translation in two directions) and reel-to-reel apparatus (for translation in one direction) such as those used in manufacturing high-density surface mount electronics assemblies. The positioning support is operable to control spacings between the impact points of the fluid drops to form discrete probes on the substrate. While the distance between the probe centers can vary, a center-to-center distance of twenty-five micrometers (25 µm) to one millimeter (1 mm) is preferred with a distance of twenty-five micrometers (25 µm) to five hundred micrometers (500 µm) being most preferred. The positioning support 84 shown in FIG. 1 comprises a first positioning system 84a which is connected to controller 70 through drive electronics 72 all of which are conventional. A single controller 70 and drive electronics 72 is shown for clarity of illustration. Obviously, multiple controllers and drive electronics may be used to control the various components.

A single printed fluid array may require a very large number (up to 1000, for example) of reagent fluids or probes. A corresponding number of fluid dispenser assemblies 20 is generally required to form the array. Consequently, the fluid dispenser assemblies are arranged in sets as hereinbefore described and a sufficient number of sets are provided to handle the desired number of reagents. Each set of dispenser assemblies is positioned and secured together so that they may be interchanged manually or automatically (in a manner similar to a tooling change) during fabrication of the fluid array. Each set preferably comprises four to sixteen fluid dispenser assemblies but more or fewer assemblies (outside the four to twenty range) may be used if desired.

Figure 3:
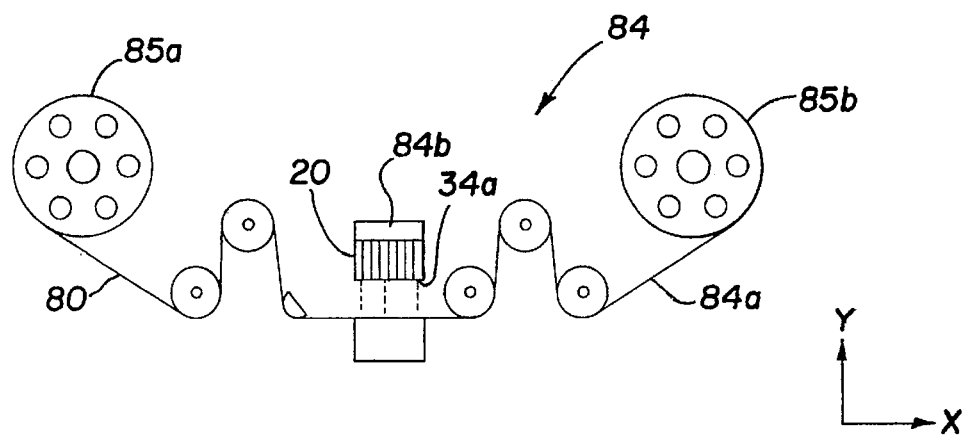
FIG. 3 is a schematic illustration of apparatus having two positioning systems for practicing the invention.

An alternative arrangement (wherein positioning support 84 combines a first and a second positioning system 84a and 84b) is illustrated in FIG. 3. First positioning system 84a is a reel-to-reel system in which substrate 80 moves from feeder reel 85a to take-up reel 85b. A plurality of fluid dispenser assemblies 20 are affixed to second positioning support 84b with outlets 34a directed toward substrate 80. First positioning system 84a translates substrate 80 along the X axis and second positioning system 84b translates the dispensers along the axis (not shown) to yield relative two dimensional movement. The components in FIG. 3 are connected to a suitable conventional controller and drive electronics as described above.

Figure 4:
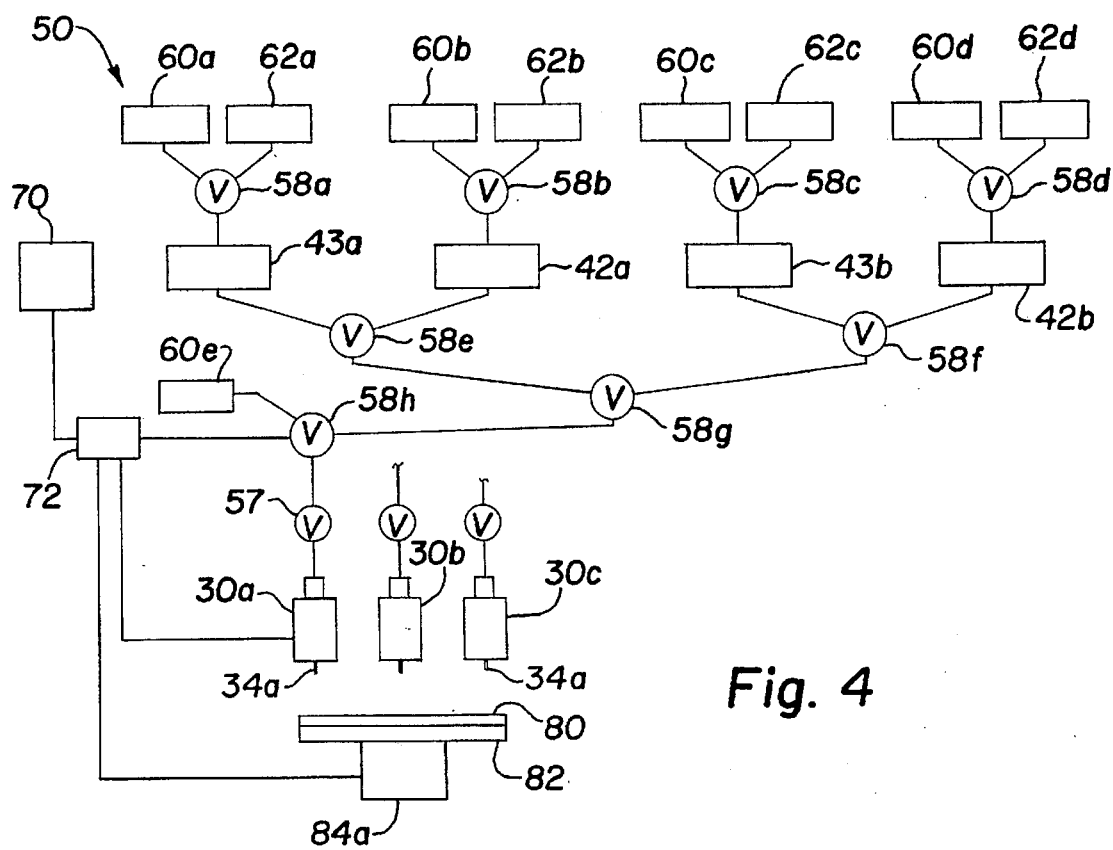
FIG. 4 is a diagrammatic illustration of alternative apparatus for forming printed fluid arrays in accordance with the invention.

FIG. 4 illustrates a system wherein the number of reservoirs is greater than the number of ejection devices and wherein the fluid handling system places a plurality of reservoirs in fluid communication with a single ejection device. This arrangement permits dispensing large numbers of fluids without using a corresponding number of ejection devices. Ejection devices 30a–30c are positioned with their outlets 34a fixed in spatial relationship relative to each other. Preferably four to twenty ejection devices 30 are similarly arranged in each array but more or fewer (outside the four to twenty range) can be used if desired.

Substrate 80 is positioned on substrate support 82 below ejection devices 30a–30c which are oriented with their outlets 34a toward substrate 80. The orientation depicted in FIG. 4 is for convenience of illustration only. Alternative embodiments may be used to position substrate 80 beside or above ejection devices 30 with outlets 34a oriented accordingly. The apparatus may include a first positioning system 84a as shown, a second positioning system (not shown) or a combination of first and second positioning systems similar to that illustrated in FIG. 1 and FIG. 3.

Fluid handling system 50 comprises reagent reservoirs 42a and 42b, solvent reservoirs 43a and 43b, positive pressure supplies 60a–60e, atmospheric pressure supplies 62a–62d, solenoid valves 58a–58h and is connected to ejection device 30a through cutoff valve 57. Solenoid valves 58a–58h operate to sequentially connect the reservoirs and pressure supplies to ejection device 30 in a desired or predetermined sequence. Additional solvent and reagent reservoirs may be added to the fluid handling means by adding the appropriate tubing, valves and pressure supplies.

The arrangement and connection of the various components in FIG. 4 is for illustrative purposes only. Various other arrangements may be used. For example, a plurality of reagent reservoirs and a single solvent source may feed into a fluid manifold or a single reagent reservoir (such as 42a) can be automatically or manually replaced with additional reagent reservoirs.

Figure 5:
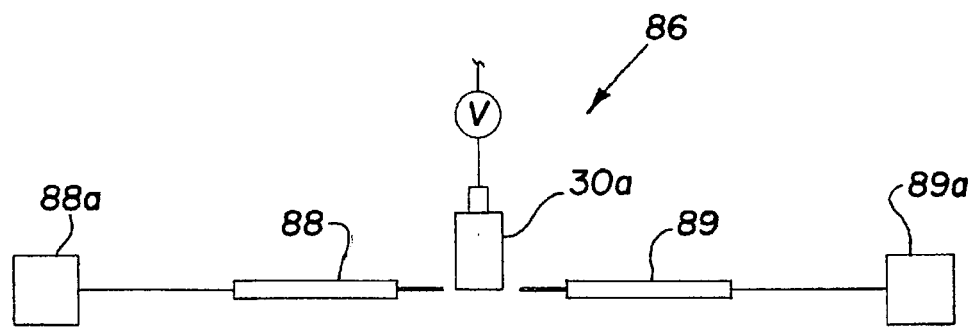
FIG. 5 is a schematic illustration of an external purging system.

FIG. 5 illustrates an external purging system 86 which comprises a nozzle 88 connected to a positive pressure supply 88a and a nozzle 89 connected to a solvent supply 89a. Nozzles 88 and 89 are positioned to direct their respective fluids onto the external portions of ejection device 30a. The exterior purging system 86 may be incorporated into the fluid handling system 50 if desired. Alternatively, the exterior purging system may be independent and automatically or manually operated.

Figure 6:
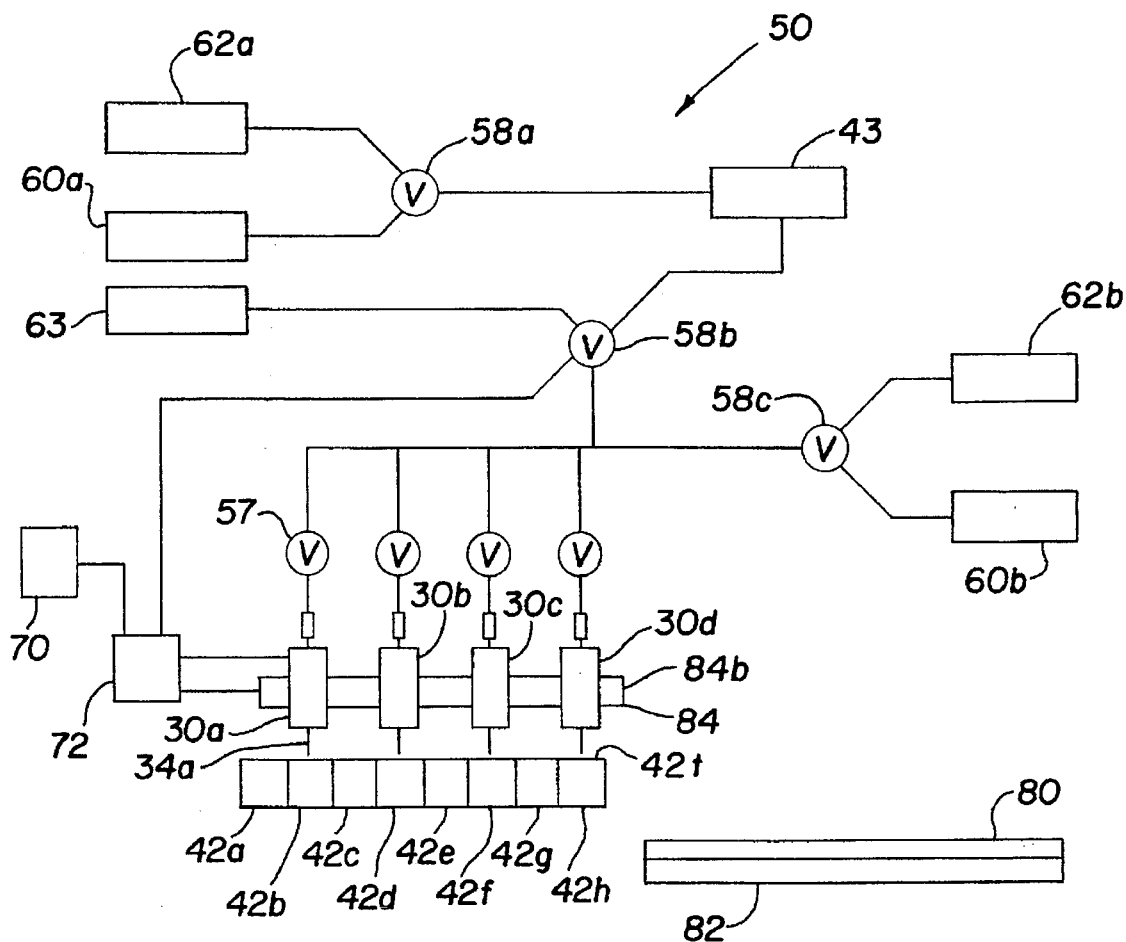
FIG. 6 is a diagrammatic illustration of an alternative embodiment of apparatus for forming miniature arrays in accordance with the invention.

FIG. 6 illustrates an embodiment wherein the number of reservoirs is greater than the number of ejection devices and wherein the positioning support cooperates with a fluid handling system to sequentially place ejection devices in communication with a plurality of fluid reservoirs. This arrangement permits dispensing large numbers of fluids without using a corresponding number of ejection devices. It also minimizes the amount of reagent which is wasted during the fabrication process because, as described hereafter, there are no fluid lines connecting the reservoirs to the ejection devices.

Ejection devices 30a–30d are fixed in spatial relationship relative to each other with their outlets 34a positioned to propel drops downward. Substrate 80 is positioned on substrate support 82 below and beside ejection devices 30a–30d. Reagent reservoirs 42a–42h are positioned below the ejection devices. Reservoirs 42a–42h are spaced relative to each other similarly to the ejection devices and the top 42t of each reservoir is open to allow access for outlets 34a.

The number and orientation of parts depicted in FIG. 6 is for convenience of illustration only. The ejection devices are connected to a positioning support comprising a second positioning system 84b. A first positioning system (not shown) can be connected to the substrate support 82 and a combination of a first and a second positioning system may be used. Ejection devices 30 are connected to the fluid handling system 50 at cutoff valve 57. Preferably, the tubing connecting the ejection devices to the cutoff valve 57 is flexible, thus allowing the ejection devices to translate while the fluid handling system 50 otherwise remains stationary.

The fluid handling system 50 comprises a plurality of solenoid valves 58a–58c, at least one solvent reservoir 43 and sources of atmospheric pressure 62a–62b, positive pressure 60a–60b, and negative pressure 63. The solenoid valves, ejection devices and positioning supports are connected to drive electronics 72 and controller 70 similarly to embodiments hereinabove described. An external purging system (not shown) similar to that shown in FIG. 5 may be included.

In the apparatus of FIG. 1 the reservoirs in a first set of fluid dispenser assemblies are filled with a first set of reagents. Solenoid valve 58 connects reservoir 42a to reservoir 42, thus enabling positive pressure 60b to force reagent from reservoir 42a into reservoir 42, through tubing 52 and into ejection device 30. End 56a is disconnected from fill port 44 and reservoir 42 is maintained at atmospheric pressure.

Controller 70 signals drive electronics 72 to send a series of activation signals to the electro-mechanical transducers 32. Transducers 32 respond to each signal by inducing a volumetric change in the ejection device 30 sufficient to propel a single drop of fluid from outlet 34a and to substrate 80. As each drop is ejected, reagent from reservoir 42 is drawn into ejection device 30 through capillary action or siphoning.

The controller 70 simultaneously operates drive electronics 72 to reposition substrate 80 at various predetermined positions. The substrate can be positioned to place a single drop of fluid at each location, for example, as when a probe is formed from a presynthesized reagent which does not require an activator fluid to couple to the substrate. Alternatively, drops of different reagents can be printed, one over the other, as when a probe is synthesized on site from multiple reagents. The term "probe" as used herein refers to both a single drop or multiple drops of fluid which have been deposited at one location on the substrate and includes situations where multiple drops have been deposited during the various stages of an on site synthesis process. For example, the first fluid dispensed at one location may be an activator fluid which permits or promotes the next reagent to couple with the surface of the substrate. The next reagent may be one of the four nucleotides which form the base sequence in a DNA molecule. Subsequent drops may be more nucleotides, activator fluids, inhibitor fluids, etc., used to synthesize in place a portion of a DNA molecule. The same process may be used to synthesize peptides in place, for example, by depositing the appropriate amino acids, activator fluids and inhibitor fluids. Probes thus formed remain discrete entities whether or not they comprise single or multiple drops.

After a desired quantity of reagent is dispensed from the reservoirs 42, the first set of dispenser assemblies is removed and replaced with another set of dispenser assemblies filled with another set of reagent fluids. The foregoing process is repeated until the diagnostic array is complete. The array thus formed can have virtually any pattern of discrete probes which is fixed by simultaneously controlling the size of the drops, the time at which they are formed and movement of the substrate with respect to the ejection devices. For example, patterns can be formed wherein the distance between the centers of the probes is maintained as small as twenty-five micrometers (25 μm). The center-to-center distances may be varied within the pattern, for example, from twenty-five micrometers (25 μm) to one millimeter (1 mm).

Since the dispenser assemblies are arranged in removable sets, any number of sets may be provided to form the desired number of probes on a single test strip. Thus, by maintaining a five hundred micrometers (500 μm) center-to-center spacing between the probes and the appropriate number of sets of dispenser assemblies and reagent fluids, an array with up to four hundred probes per square centimeter can be formed. Furthermore, a twenty-five micrometer (25 μm) center-to-center spacing between probes along with the appropriate number of sets can easily produce an array having a thousand probes per square centimeter.

The arrangement of FIG. 3 operates similarly to that illustrated in FIG. 1 except that the controller and drive electronics operate both a first and a second positioning system 84a and 84b. Each drop issued from the ejection devices is accurately positioned on the substrate at a known location by moving the ejection devices on the Y axis and by moving the substrate on the X axis.

In the arrangement illustrated in FIG. 4, reagent reservoirs 42a and 42b are filled with different reagents. Controller 70 signals drive electronics 72 to position solenoid valves 58b, 58e, 58g and 58h to permit positive pressure supply 60b to force the reagent in reservoir 42a into ejection device 30a. Controller 70 also signals drive electronics 72 to send a predetermined series of activation signals to the ejection device 30a. The ejection device propels drops of fluid through the outlet 34a to the substrate 80 while the substrate is simultaneously moved to various positions as hereinbefore described.

After a desired quantity of reagent is dispensed from reservoir 42a, the controller and drive electronics position solenoid valves 58a, 58e, 58g and 58h to permit positive pressure supply 60a to force solvent from reservoir 43a through the lines, valves and ejection devices to purge the first reagent from the internal portions of the system. Nozzle 89 is positioned to simultaneously spray the external surfaces of the ejection device.

After a purging period suitable to clean the first reagent from the system, solenoid valve 58h connects positive pressure supply 60e with the ejection device to evaporate the solvent from inside the apparatus. Nozzle 88 is positioned to simultaneously dry the external surfaces of the system. After the reagent is purged from the apparatus, the appropriate solenoid valves are positioned to repeat the process with reagent from reservoir 42b and solvent from reservoir 43b. The fluid handling system places selected reservoirs in communication with selected ejection devices in a desired or predetermined sequence until the printed fluid array is complete. The sequence of filling and purging may be varied. For example, the filling and purging operations may occur simultaneously at all ejection devices or some devices may undergo the purging process while others are propelling fluid towards the substrate.

In the arrangement illustrated in FIG. 6, positioning support 84b and fluid handling systems 50 cooperate to place the ejection devices 30a–30d in fluid communication with the reservoirs 42a–42h. Reservoirs 42a–42h are filled with a plurality of reagent fluids and positioning support 84b places ejection devices 30a–30d over reservoirs 42b, 42d, 42f and 42h. Since the reservoirs are spaced similarly to the ejection devices, outlets 34a are each positioned over a single reservoir. The outlets 34a are immersed in their respective reservoirs through top 42t and controller 70 signals drive electronics 72 to connect negative pressure supply 63 to the ejection devices so that a predetermined quantity of reagent is drawn into the ejection devices 30a–30d from the reservoirs. After the ejection devices are filled, positioning support 84b positions the devices over the substrate 80. Drops of reagent are propelled from each ejection device while the substrate is moved to different positions as hereinbefore described. After a predetermined quantity of reagent is dispensed, solenoid valves 58a and 58b are operated to connect the ejection device with solvent in reservoir 43. Positive pressure 60a forces solvent through the ejection devices 30a–30d to purge the first reagent from the system and nozzle 88 is positioned to simultaneously spray the external surfaces of the ejection devices.

After the first reagent is purged from the system, solenoid valve 58c connects positive pressure 60b with the ejection device to evaporate the solvent. When the solvent has evaporated, positioning support 84 positions the ejection devices over reservoirs 42a, 42c, 42e and 42g and the process is repeated. The fluid handling system continues to place predetermined reservoirs in communication with predetermined ejection devices in a predetermined sequence until the printed fluid array is complete. The sequence of filling and purging operations may be varied as hereinbefore described.

From the foregoing it will be recognized that the principles of the invention may be employed in various arrangements to obtain the benefits of the advantages and features disclosed. It is to be understood, therefore, that although numerous characteristics and advantages of the invention have been set forth together with details of the structure and function of various embodiments of the invention, this disclosure is illustrative only. Various changes and modifications may be made in detail, especially in matters of shape, size and arrangement of parts, without departing from the spirit and scope of the invention as defined by the appended claims.

What is claimed:

1. A method of forming diagnostic arrays having a number of discrete probes to produce a test strip on a substrate surface suitable for exposure to a sample of unknown substance, comprising the steps of:
    (a) positioning a test strip substrate on a controllably movable substrate support;
    (b) positioning over the substrate, a first replaceable set of electro-mechanical fluid ejection devices each having an outlet in fixed spatial relationship relative to each other with said outlets oriented toward the surface of the substrate;
    (c) placing activator and test probe fluids in respective reservoirs of a first set of reservoirs, each reservoir being in communication with one of the ejection devices in said first replacement set; and
    (d) activating the ejection devices in said first replaceable set and moving said test strip substrate relative to said ejection devices to form and position drops of activator fluid from said first set of reservoirs on the test strip substrate surface in a pattern of discrete sites established by the ejection devices in said first replaceable set, and moving said test strip relative to said ejection devices to form and position drops of test probe fluids from said first set of reservoirs on the test strip surface, on said pattern of sites to form a pattern of discrete test probes, wherein each probe is formed from at least one test probe fluid whereby a test strip having a desired pattern of test probes is prepared for use.

2. A method as set forth in claim 1 including the steps of:
    (e) replacing said first replaceable set of ejection devices with a second replaceable set of electro-mechanical fluid ejection devices having outlets in fixed spacial relationship relative to each other with said outlets oriented toward the surface of the substrate;
    (f) placing a test probe fluid in each of a second set of reservoirs and each reservoir in communication with one of the ejection devices in said second replaceable set; and
    (g) activating the ejection devices in said second replaceable set to form and position drops of test probe fluids from said second set of reservoirs on the surface of said substrate to form a test strip having test probes formed from test probe fluid supplied by each of said replaceable sets of ejection devices.

3. A method as set forth in claim 2 wherein at least some of the drops of test probe fluids from said second set of reservoirs are placed on discrete probes formed of test probe fluids from said first set of reservoirs.

4. A method as set forth in claim 2 wherein steps e–g are repeated with at least a third replaceable set of ejection devices and at least a third set of reservoirs.

5. A diagnostic test strip array formed by the process of claim 2.

6. A method as set forth in claim 2 wherein said pattern of discrete probes comprises at least about 400 probes per square centimeter.

7. A method as set forth in claim 2 wherein said pattern of discrete probes comprises at least about 1000 probes per square centimeter.

8. A method of forming diagnostic arrays having a number of discrete test probes on a substrate surface comprising the steps of:
    (a) positioning a substrate on a substrate support;
    (b) positioning a plurality of electro-mechanical fluid ejection devices having outlets in fixed spacial relationship relative to each other with said outlets oriented toward the substrate;
    (c) providing plurality of fluid reservoirs greater in number than the plurality of electro-mechanical fluid ejection devices and a fluid handling system which selectively places each of the plurality of reservoirs in fluid communication with selected ones of the plurality of fluid ejection devices;
    (d) placing a fluid in each of a plurality of reservoirs;
    (e) placing a selected one of the plurality of fluid ejection devices in fluid communication with one fluid reservoir of said plurality of fluid reservoirs;
    (f) activating said selected one of the plurality of fluid ejection devices and moving said substrate support relative to said selected ejection devices to form and position drops of fluid from said one fluid reservoir into a pattern of discrete test probes on said substrate;
    (g) placing the selected one of the plurality of fluid ejection devices in fluid communication with another fluid reservoir of said plurality of fluid reservoirs; and
    (h) activating said selected one of the plurality of fluid ejection devices and moving said substrate support relative to said selected ejection devices to form and position drops of fluid from said another fluid reservoir into a pattern of discrete test probes on said substrate;
    (i) whereby a plurality of fluids can be dispensed from said reservoirs to form discrete test probes on said substrate without having the number of fluid ejection devices corresponding to the number of fluid reservoirs.

9. A method as set forth in claim 8 wherein said ejection devices are placed in communication with said reservoirs by immersing said outlets in the fluids in said reservoirs and applying negative pressure to said ejection devices to draw fluids into said ejection devices through said outlets.

10. A method as set forth in claim 8 wherein said ejection devices are placed in communication with said reservoirs by positioning a plurality of valves to place a positive pressure supply in communication with said reservoirs to urge fluids therein into said ejection devices.

11. A method as set forth in claim 8 wherein each of said drops of fluid has a volume of from about 10 pl to about 1 nl.

12. A method as set forth in claim 8 wherein the center-to-center spacing between probes is from about 1 millimeter to about twenty-five micrometers.

13. The diagnostic array formed by the process of claim 12.

14. A method as set forth in claim 8 wherein said pattern of discrete probes comprises at least about 400 probes per square centimeter.

15. A method as set forth in claim 8 wherein said pattern of discrete probes comprises at least about 1000 probes per square centimeter.

16. A method as set forth in claim 8 wherein each ejection device dispenses a solvent after dispensing the fluid from said reservoir but before dispensing the fluid from the next said reservoir sequentially placed in communication with said ejection device.

17. A method as set forth in claim 8 wherein an exterior surface of each dispensing device is sprayed with a solvent after dispensing the fluid from said reservoir but before dispensing the fluid from the next said reservoir sequentially placed in communication with said ejection device.

18. Apparatus for forming diagnostic arrays comprising a number of discrete probes to produce a test strip on a substrate surface suitable for exposure to a sample of unknown substance comprising:

(a) a substrate support;

(b) a test strip substrate positioned on said support;

(c) a plurality of electro-mechanical fluid ejection devices having outlets positioned in fixed spatial relationship relative to each other with said outlets oriented toward the test strip substrate and moveable with respect to said substrate support;

(d) a plurality of test probe fluid reservoirs greater in number than said plurality of electro-mechanical ejection devices;

(e) a fluid handling means for selectively placing each one of said plurality of fluid reservoirs individually in communication with at least one of said ejection devices;

(f) means for activating said at least one ejection devices to propel drops of test probe fluid from a selected one of said plurality of test probe fluid reservoirs toward the substrate; and (g) means for moving said ejection devices and the substrate relative to each other to form a pattern of discrete test probes formed from selected ones of the plurality of test probe fluid reservoirs on the substrate.

19. Apparatus as defined in claim 18 wherein said outlets are sized to produce drops of test probe liquid having a volume between about 10 pl and about 1 nl.

20. Apparatus as defined in claim 18 wherein said placement means positions the impact points of multiple test probe fluid drops on the substrate to within a range of about twenty-five micrometers to about 1 millimeter.

21. Apparatus as defined in claim 18 wherein said placement means and said ejection devices are operable to place about 400 different test probes in an area of about one square centimeter.

22. Apparatus as defined in claim 18 wherein said placement means and said ejection devices are operable to place about 1000 different test probes in an area of about one square centimeter.

23. Apparatus as defined in claim 18 wherein a substantially equal number of said ejection devices and said reservoirs are provided; and wherein said fluid handling means places a single reservoir in communication with a single ejection device.

24. Apparatus as defined in claim 18 wherein said fluid handling means comprises:

(i) at least one positive pressure supply; and (ii) a plurality of valves connecting said positive pressure supply to at least some of said reservoirs in a selected sequence to urge the fluid in said reservoirs into said ejection devices.

25. Apparatus as defined in claim 24 having a first solvent supply connected to said fluid handling means for purging an internal portion of the apparatus.

26. Apparatus as defined in claim 25 having a second solvent supply and at least one nozzle positioned to direct solvent from said second solvent supply onto an external portion of the apparatus.

27. Apparatus as defined in claim 18 wherein said placement means is operable to selectively immerse said outlets in fluids in said reservoirs; and wherein said fluid handling means comprises at least one negative pressure supply and a plurality of valves selectively connecting said negative pressure supply to at least some of said ejection devices to draw the fluid in said reservoirs into said ejection devices through said outlets.

28. Apparatus as defined in claim 27 including a first solvent supply connected to said fluid handling means for purging an internal portion of the apparatus.

29. Apparatus as defined in claim 28 including a second solvent supply and at least one nozzle positioned to direct solvent from said second solvent supply onto an external portion of the apparatus.

* * * * *